(12) United States Patent
Olah et al.

(10) Patent No.: US 7,605,293 B2
(45) Date of Patent: *Oct. 20, 2009

(54) EFFICIENT AND SELECTIVE CONVERSION OF CARBON DIOXIDE TO METHANOL, DIMETHYL ETHER AND DERIVED PRODUCTS

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 298 days.

This patent is subject to a terminal disclaimer.

(21) Appl. No.: 11/402,050

(22) Filed: Apr. 12, 2006

(65) Prior Publication Data

US 2006/0235091 A1    Oct. 19, 2006

Related U.S. Application Data

(60) Provisional application No. 60/671,651, filed on Apr. 15, 2005, provisional application No. 60/763,678, filed on Jan. 30, 2006.

(51) Int. Cl.
*C07C 29/51* (2006.01)
*C07C 29/15* (2006.01)
*C07C 29/132* (2006.01)

(52) U.S. Cl. .................... 568/885; 568/884; 518/726

(58) Field of Classification Search ............. 568/885, 568/884; 518/726
See application file for complete search history.

(56) References Cited

U.S. PATENT DOCUMENTS

| | | | | | |
|---|---|---|---|---|---|
| 3,236,762 | A | * | 2/1966 | Rabo et al. ............ 208/111.25 |
| 3,482,952 | A | * | 12/1969 | Sieg et al. ..................... 44/449 |
| 3,711,258 | A | * | 1/1973 | Matthews et al. ........... 585/733 |
| 4,364,915 | A | * | 12/1982 | Proctor ..................... 423/437.1 |
| 4,374,288 | A | * | 2/1983 | Scragg ....................... 568/910 |
| 4,607,127 | A | * | 8/1986 | Spencer ..................... 568/482 |
| 4,618,732 | A | * | 10/1986 | Gesser et al. ............ 568/910.5 |
| 4,705,771 | A | * | 11/1987 | Spencer ..................... 502/255 |
| 4,762,528 | A | | 8/1988 | Reichl ........................... 44/51 |
| 4,891,049 | A | * | 1/1990 | Dillon et al. .................. 44/387 |
| 5,349,096 | A | * | 9/1994 | Cockman et al. ............ 568/896 |
| 5,510,393 | A | * | 4/1996 | Coffman ..................... 518/703 |
| 5,571,483 | A | * | 11/1996 | Pfingstl et al. .............. 422/166 |
| 5,599,638 | A | * | 2/1997 | Surampudi et al. ............ 429/33 |
| 5,606,107 | A | * | 2/1997 | Smith .......................... 562/17 |
| 5,753,143 | A | * | 5/1998 | Bhat et al. ................... 252/373 |
| 5,928,806 | A | | 7/1999 | Olah et al. .................... 429/13 |
| 6,045,761 | A | * | 4/2000 | Bill et al. ............... 422/186.04 |
| 6,170,264 | B1 | * | 1/2001 | Viteri et al. .................. 60/671 |
| 6,232,352 | B1 | * | 5/2001 | Vidalin ....................... 518/700 |
| 6,375,832 | B1 | * | 4/2002 | Eliasson et al. ............. 208/141 |
| 6,376,254 | B1 | * | 4/2002 | Bather et al. ................ 436/140 |
| 6,531,630 | B2 | * | 3/2003 | Vidalin ....................... 562/519 |
| 6,690,180 | B2 | * | 2/2004 | Schwartz et al. ............ 324/670 |
| 6,740,434 | B2 | * | 5/2004 | Surampudi et al. ............ 429/15 |
| 6,782,947 | B2 | * | 8/2004 | de Rouffignac et al. ..... 166/245 |
| 6,881,759 | B2 | * | 4/2005 | Nielsen et al. .............. 518/705 |
| 7,081,547 | B2 | * | 7/2006 | Fujimoto et al. ............ 560/232 |
| 7,288,387 | B2 | * | 10/2007 | Cheng et al. .................. 435/67 |
| 7,375,142 | B2 | * | 5/2008 | Pearson ..................... 518/706 |
| 7,378,561 | B2 | * | 5/2008 | Olah et al. .................. 568/885 |
| 7,459,590 | B2 | * | 12/2008 | Olah et al. .................. 568/885 |
| 2006/0235088 | A1 | * | 10/2006 | Olah et al. .................. 518/702 |
| 2006/0235091 | A1 | * | 10/2006 | Olah et al. .................. 518/726 |
| 2007/0254969 | A1 | * | 11/2007 | Olah et al. .................. 518/726 |
| 2008/0039538 | A1 | * | 2/2008 | Olah et al. .................. 518/702 |

FOREIGN PATENT DOCUMENTS

| | | | |
|---|---|---|---|
| EP | 1 180 511 A1 | | 2/2002 |
| FR | 2877939 A 1 | * | 5/2006 |
| JP | 2004285187 A | * | 10/2004 |
| RU | 2104990 C 1 | * | 2/1998 |

OTHER PUBLICATIONS

Ashby, E.C. et al., "Concerning the formation of hydrogen in nuclear waste. Quantitative generation of hydrogen via a cannizzaro intermediate," J. Am. Chem. Soc. 115:1171-1173 (1993).

* cited by examiner

*Primary Examiner*—Shailendra Kumar
(74) *Attorney, Agent, or Firm*—Winston & Strawn LLP

(57) ABSTRACT

An environmentally beneficial method of producing methanol from varied sources of carbon dioxide including flue gases of fossil fuel burning powerplants, industrial exhaust gases or the atmosphere itself. Converting carbon dioxide by electrochemical reduction produces formic acid acid and some formaldehyde and methanol mixtures. The formic acid can be used as source of carbon as well as hydrogen to produce methanol, dimethyl ether and other products.

20 Claims, 2 Drawing Sheets

EFFICIENT AND SELECTIVE CONVERSION OF CARBON DIOXIDE TO METHANOL, DIMETHYL ETHER AND DERIVED PRODUCTS

This application claims the benefit of provisional applications 60/671,651 filed Apr. 15, 2005 and 60/763,678 filed Jan. 30, 2006. The content of each application is expressly incorporated herein by reference thereto.

BACKGROUND

Hydrocarbons are essential in modern life. Hydrocarbons are used as fuel and raw material in various fields, including the chemical, petrochemical, plastics, and rubber industries. Fossil fuels, such as coal, oil and gas, are composed of hydrocarbons with varying ratios of carbon and hydrogen, and is non-renewably used when combusted, forming carbon dioxide and water. Despite their wide application and high demand, fossil fuels present a number of disadvantages, including the finite reserve, irreversible combustion and contribution to air pollution and global warming. Considering these disadvantages, and the increasing demand for energy, alternative sources of energy are needed.

One such alternative frequently mentioned is hydrogen, and the so-called "hydrogen economy." Hydrogen is beneficial as a clean fuel, producing only water when combusted. Free hydrogen, however, is not a natural energy source, and its generation from hydrocarbons or water is a highly energy-consuming process. Further, when hydrogen is produced from hydrocarbons, any claimed benefit of hydrogen as a clean fuel is outweighed by the fact that generation of hydrogen itself, mainly by reforming of natural gas, oil or coal to synthesis gas ("syn-gas") a mixture of CO and $H_2$, is far from clean. It consumes fossil fuels, with a quarter of the energy of the fuel being lost as heat. Hydrogen is also not a convenient energy storage medium because it is difficult and costly to handle, store, transport and distribute. As it is extremely volatile and potentially explosive, hydrogen gas requires high-pressure equipment, costly and non-existent infrastructure, special materials to minimize diffusion and leakage, and extensive safety precautions to prevent explosions.

It was suggested that a more practical alternative is methanol. Methanol, $CH_3OH$, is the simplest liquid oxygenated hydrocarbon, differing from methane ($CH_4$) by a single additional oxygen atom. Methanol, also called methyl alcohol or wood alcohol, is a colorless, water-soluble liquid with a mild alcoholic odor, and is easy to store and transport. It freezes at −97.6° C., boils at 64.6° C., and has a density of 0.791 at 20° C.

Methanol is not only a convenient and safe way to store energy, but, together with its derived dimethyl ether (DME), is an excellent fuel. Dimethyl ether is easily obtained from methanol by dehydration and is an effective fuel particularly in diesel engines because of its high cetane number and favorable properties. Methanol and dimethyl ether can be blended with gasoline or diesel and used as fuels, for example in internal combustion engines or electricity generators. One of the most efficient use of methanol is in fuel cells, particularly in direct methanol fuel cell (DMFC), in which methanol is directly oxidized with air to carbon dioxide and water while producing electricity.

Contrary to gasoline, which is a complex mixture of many different hydrocarbons and additives, methanol is a single chemical compound. It contains about half the energy density of gasoline, meaning that two liters of methanol provides the same energy as a liter of gasoline. Even though methanol's energy content is lower, it has a higher octane rating of 100 (average of the research octane number (RON) of 107 and motor octane number (MON) of 92), which means that the fuel/air mixture can be compressed to a smaller volume before being ignited. This allows the engine to run at a higher compression ratio (10-11 to 1 against 8-9 to 1 of a gasoline engine), more efficiently than a gasoline-powered engine. Efficiency is also increased by methanol's higher "flame speed," which enables faster, more complete fuel combustion in the engines. These factors explain the high efficiency of methanol despite its lower energy density than gasoline. Further, to render methanol more ignitable even under the most frigid conditions, methanol can be mixed with gasoline, with volatile compounds (e.g., dimethyl ether), with other components or with a device to vaporize or atomize methanol. For example, an automotive fuel can be prepared by adding methanol to gasoline with the fuel having a minimum gasoline content of at least 15% by volume (M85 fuel) so that it can readily start even in low temperature environments. Of course, any replacement of gasoline in such fuels will conserve oil resources, and the amount of methanol to add can be determined depending upon the specific engine design.

Methanol has a latent heat of vaporization of about 3.7 times higher than gasoline, and can absorb a significantly larger amount of heat when passing from liquid to gas state. This helps remove heat away from the engine and enables the use of an air-cooled radiator instead of a heavier water-cooled system. Thus, compared to a gasoline-powered car, a methanol-powered engine provides a smaller, lighter engine block, reduced cooling requirements, and better acceleration and mileage capabilities. Methanol is also more environment-friendly than gasoline, and produces low overall emissions of air pollutants such as hydrocarbons, $NO_x$, $SO_2$ and particulates.

Methanol is also one of the safest fuels available. Compared to gasoline, methanol's physical and chemical properties significantly reduce the risk of fire. Methanol has lower volatility, and methanol vapor must be four times more concentrated than gasoline for ignition to occur. Even when ignited, methanol burns about four times slower than gasoline, releases heat only at one-eighth the rate of gasoline fire, and is far less likely to spread to surrounding ignitable materials because of the low radiant heat output. It has been estimated by the EPA that switching from gasoline to methanol would reduce incidence of fuel-related fire by 90%. Methanol burns with a colorless flame, but additives can solve this problem.

Methanol also provides an attractive and more environment-friendly alternative to diesel fuel. Methanol does not produce smoke, soot, or particulates when combusted, in contrast to diesel fuel, which generally produces polluting particles during combustion. Methanol also produces very low emissions of NOx because it burns at a lower temperature than diesel. Furthermore, methanol has a significantly higher vapor pressure compared to diesel fuel, and the higher volatility allows easy start even in cold weather, without producing white smoke typical of cold start with a conventional diesel engine. If desired, additives or ignition improvers, such as octyl nitrate, tetrahydrofurfuryl nitrate, peroxides or higher alkyl ethers, can be added to bring methanol's cetane rating to the level closer to diesel. Methanol can also be used in the manufacture of biodiesel fuels by esterification of fatty acids.

Closely related and derived from methanol, and also a desirable alternative fuel is dimethyl ether. Dimethyl ether (DME, $CH_3OCH_3$), the simplest of all ethers, is a colorless, nontoxic, non-corrosive, non-carcinogenic and environmentally friendly chemical that is mainly used today as an aerosol propellant in spray cans, in place of the banned CFC gases. DME has a boiling point of −25° C., and is a gas under ambient conditions. DME is, however, easily handled as liquid and stored in pressurized tanks, much like liquefied petroleum gas (LPG). The interest in dimethyl ether as alternative fuel lies in its high cetane rating of 55 to 60, which is much higher than that of methanol and is also higher than the cetane rating of 40 to 55 of conventional diesel fuels. The cetane rating indicates that DME can be effectively used in diesel engines. Advantageously, DME, like methanol, is clean burning, and produces no soot particulates, black smoke or $SO_2$, and only very low amounts of $NO_x$ and other emissions even without after-treatment of its exhaust gas. Some of the physical and chemical properties DME, in comparison to diesel fuel, are shown in Table 1.

TABLE 1

Comparison of the physical properties of DME and diesel fuel

|  | DME | Diesel fuel |
| --- | --- | --- |
| Boiling point ° C. | −24.9 | 180-360 |
| Vapor pressure at 20° C. (bar) | 5.1 | — |
| Liquid density at 20° C. (kg/m$^3$) | 668 | 840-890 |
| Heating value (kcal/kg) | 6,880 | 10,150 |
| Cetane number | 55-60 | 40-55 |
| Autoignition temperature (° C.) | 235 | 200-300 |
| Flammability limits in air (vol %) | 3.4-17 | 0.6-6.5 |

Currently, DME is exclusively produced by dehydration of methanol. A method for synthesizing DME directly from synthesis gas by combining the methanol synthesis and dehydration steps in a single process has also been developed.

Another methanol derivative is dimethyl carbonate (DMC), which can be obtained by converting methanol with phosgene or by oxidative carbonylation of the methanol. DMC has a high cetane rating, and can be blended into diesel fuel in a concentration up to 10%, reducing fuel viscosity and improving emissions.

Methanol and its derivatives, e.g., DME, DMC, and biodiesel, have many existing and potential uses. They can be used, for example, as a substitute for gasoline and diesel fuel in ICE-powered cars with only minor modifications to the existing engines and fuel systems. Methanol can also be used in fuel cells, for fuel cell vehicles (FCVs), which are considered to be the best alternative to ICEs in the transportation field. DME is also a potential substitute for LNG and LPG for heating homes and in industrial uses.

Methanol is also useful in reforming to hydrogen. In an effort to address the problems associated with hydrogen storage and distribution, suggestions have been made to use liquids rich in hydrogen such as gasoline or methanol as a source of hydrogen in vehicles via an on-board reformer. It is also considered that methanol is the safest of all materials available for such hydrogen production. Further, because of the high hydrogen content of liquid methanol, even compared to pure cryogenic hydrogen (98.8 g of hydrogen in a liter of methanol at room temperature compared to 70.8 g in liquid hydrogen at −253° C.), methanol is an excellent carrier of hydrogen fuel. The absence of C—C bonds in methanol, which are difficult to break, facilitates its transformation to pure hydrogen with 80 to 90% efficiency.

In contrast to a pure hydrogen-based storage system, a reformer system is compact, containing on a volume basis more hydrogen than even liquid hydrogen, and is easy to store and handle without pressurization. A methanol steam reformer is also advantageous in allowing operation at a much lower temperature (250-350° C.) and for being better adapted to on-board applications. Furthermore, methanol contains no sulfur, a contaminant for fuel cells, and no nitrogen oxides are formed from a methanol reformer because of the low operating temperature. Particulate matter and $NO_x$ emissions are virtually eliminated, and other emissions are minimal. Moreover, methanol allows refueling to be as quick and easy as with diesel fuel. Thus, an on-board methanol reformer enables rapid and efficient delivery of hydrogen from liquid fuel that can be easily distributed and stored in the vehicle. To date, methanol is the only liquid fuel that has been processed and demonstrated on a practical scale as suitable for use in a fuel cell for transportation applications.

In addition to on-board reforming, methanol also enables convenient production of hydrogen in fueling stations for refueling hydrogen fuel cell vehicles. A fuel cell, an electrochemical device that converts free chemical energy of fuel directly into electrical energy, provides a highly efficient way of producing electricity via catalytic electrochemical oxidation. For example, hydrogen and oxygen (air) are combined in an electrochemical cell-like device to produce water and electricity. The process is clean, with water being the only byproduct. However, because hydrogen itself must first be produced in an energy-consuming process, by electrolysis or from a hydrocarbon source (fossil fuel) with a reformer, hydrogen fuel cells are still necessarily limited in utility.

A system for producing high purity hydrogen has been developed by steam reforming of methanol with a highly active catalyst, which allows operation at a relatively low temperature (240-290° C.) and enables flexibility in operation as well as rapid start-up and stop. These methanol-to-hydrogen (MTH) units, ranging in production capacity from 50 to 4000 m$^3$ H$_2$ per hour, are already used in various industries, including the electronic, glass, ceramic, and food processing industries, and provide excellent reliability, prolonged life span, and minimal maintenance. Operating at a relatively low temperature, the MTH process has a clear advantage over reforming of natural gas and other hydrocarbons which must be conducted at above 600° C., because less energy is needed to heat methanol to the appropriate reaction temperature.

The usefulness of methanol has led to development of other reforming processes, for example, a process known as oxidative steam reforming, which combines steam reforming, partial oxidation of methanol, and novel catalyst systems. Oxidative steam reforming produces high purity hydrogen with zero or trace amounts of CO, at high methanol conversion and temperatures as low as 230° C. It has the advantage of being, contrary to steam reforming, an exothermic reaction, therefore minimizing energy consumption. There is also autothermal reforming of methanol, which combines steam reforming and partial oxidation of methanol in a specific ratio and addresses any drawback of an exothermic reaction by producing only enough energy to sustain itself. Autothermal reforming is neither exothermic nor endothermic, and does not require any external heating once the reaction temperature is reached. Despite the aforementioned possibilities, hydrogen fuel cells must use highly volatile and flammable hydrogen or reformer systems.

U.S. Pat. No. 5,599,638 discloses a simple direct methanol fuel cell (DMFC) to address the disadvantages of hydrogen fuel cells. In contrast to a hydrogen fuel cell, the DMFC is not dependent on generation of hydrogen by processes such as electrolysis of water or reformation of natural gas or hydrocarbon. The DMFC is also more cost effective because methanol, as a liquid fuel, does not require cooling at ambient temperatures or costly high pressure infrastructure and can be used with existing storage and dispensing units, unlike hydrogen fuel, whose storage and distribution requires new infrastructure. Further, methanol has a relatively high theoretical volumetric energy density compared to other systems such as conventional batteries and the $H_2$-PEM fuel cell. This is of great importance for small portable applications (cellular phones, laptop computers, etc.), for which small size and weight of energy unit is desired.

The DMFC offers numerous benefits in various areas, including the transportation sector. By eliminating the need for a methanol steam reformer, the DMFC significantly reduces the cost, complexity and weight of the vehicle, and improves fuel economy. A DMFC system is also comparable in its simplicity to a direct hydrogen fuel cell, without the cumbersome problems of on-board hydrogen storage or hydrogen producing reformers. Because only water and $CO_2$ are emitted, emissions of other pollutants (e.g., $NO_x$, PM, $SO_2$, etc.) are eliminated. Direct methanol fuel cell vehicles are expected to be virtually zero emission vehicles (ZEV), and use of methanol fuel cell vehicles offers to nearly eliminate air pollutants from vehicles in the long term. Further, unlike ICE vehicles, the emission profile is expected to remain nearly unchanged over time. New membranes based on hydrocarbon or hydrofluorocarbon materials with reduced cost and crossover characteristics have been developed that allow room temperature efficiency of 34%.

Methanol as indicated provides a number of important advantages as transportation fuel. Contrary to hydrogen, methanol does not require any energy intensive procedures for pressurization or liquefaction. Because it is a liquid at room temperature, it can be easily handled, stored, distributed and carried in vehicles. It can act as an ideal hydrogen carrier for fuel cell vehicles through on-board methanol reformers, and can be used directly in DMFC vehicles.

Methanol is also an attractive source of fuel for static applications. For example, methanol can be used directly as fuel in gas turbines to generate electric power. Gas turbines typically use natural gas or light petroleum distillate fractions as fuel. Compared to such fuels, methanol can achieve higher power output and lower $NO_x$ emissions because of its lower flame temperature. Since methanol does not contain sulfur, $SO_2$ emissions are also eliminated. Operation on methanol offers the same flexibility as on natural gas and distillate fuels, and can be performed with existing turbines, originally designed for natural gas or other fossil fuels, after relatively easy modification. Methanol is also an attractive fuel since fuel-grade methanol, with lower production cost than higher purity chemical-grade methanol, can be used in turbines. Because the size and weight of a fuel cell is of less importance in static applications than mobile applications, various fuel cells other than PEM fuel cells and DMFC, such as phosphoric acid, molten carbonate and solid oxide fuel cells (PAFC, MCFC, and SOFC, respectively), can also be used.

In addition to use as fuels, methanol and methanol-derived chemicals have other significant applications in the chemical industry. Today, methanol is one of the most important feedstock in the chemical industry. Most of the 32 million tons of annually produced methanol is used to manufacture a large variety of chemical products and materials, including basic chemicals such as formaldehyde, acetic acid, MTBE (although it is increasingly phased out for environmental reasons), as well as various polymers, paints, adhesives, construction materials, and others. Worldwide, almost 70% of methanol is used to produce formaldehyde (38%), methyl-tert-butyl ether (MTBE, 20%) and acetic acid (11%). Methanol is also a feedstock for chloromethanes, methylamines, methyl methacrylate, and dimethyl terephthalate, among others. These chemical intermediates are then processed to manufacture products such as paints, resins, silicones, adhesives, antifreeze, and plastics. Formaldehyde, produced in large quantities from methanol, is mainly used to prepare phenol-, urea- and melamine-formaldehyde and polyacetal resins as well as butanediol and methylene bis(4-phenyl isocyanate) (MDI; MDI foam is used as insulation in refrigerators, doors, and in car dashboards and bumpers). Formaldehyde resins are predominantly employed as an adhesive in a wide variety of applications, e.g., manufacture of particle boards, plywood and other wood panels. Examples of methanol-derived chemical products and materials are shown in FIG. 1.

In producing basic chemicals, raw material feedstock constitutes typically up to 60-70% of the manufacturing costs. The cost of feedstock therefore plays a significant economic role. Because of its lower cost, methanol is considered a potential feedstock for processes currently utilizing more expensive feedstocks such as ethylene and propylene, to produce chemicals including acetic acid, acetaldehyde, ethanol, ethylene glycol, styrene, and ethylbenzene, and various synthetic hydrocarbon products. For example, direct conversion of methanol to ethanol can be achieved using a rhodium-based catalyst, which has been found to promote the reductive carbonylation of methanol to acetaldehyde with selectivity close to 90%, and a ruthenium catalyst, which further reduces acetaldehyde to ethanol. The possibility of producing ethylene glycol via methanol oxidative coupling instead of the usual process using ethylene as feedstock is also pursued, and significant advances for synthesizing ethylene glycol from dimethyl ether, obtained by methanol dehydration, have also been made.

Conversion of methanol to olefins such as ethylene and propylene, also known as methanol to olefin (MTO) technology, is particularly promising considering the high demand for olefin materials, especially in polyolefin production. The MTO technology is presently a two-step process, in which natural gas is converted to methanol via syn-gas and methanol is then transformed to olefin. It is considered that methanol is first dehydrated to dimethyl ether (DME), which then reacts to form ethylene and/or propylene. Small amounts of butenes, higher olefins, alkanes, and aromatics are also formed.

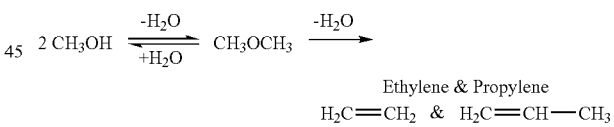

Various catalysts, e.g., synthetic aluminosilicate zeolite catalysts, such as ZSM-5 (a zeolite developed by Mobil), silicoaluminophosphate (SAPO) molecular sieves such as SAPO-34 and SAPO-17 (UOP), as well as bi-functional supported acid-base catalysts such as tungsten oxide over alumina ($WO_3/Al_2O_3$), have been found to be active in converting methanol to ethylene and propylene at a temperature between 250 and 350° C. The type and amount of the end product depend on the type of the catalyst and the MTO process used. Depending on the operating conditions, the weight ratio of propylene to ethylene can be modified between about 0.77 and 1.33, allowing considerable flexibility. For example, when using SAPO-34 according to an MTO process developed by UOP and Norsk Hydro, methanol is converted to ethylene and propylene at more than 80% selectivity, and also to butene, a valuable starting material for a number of products, at about 10%. When using an MTO process developed by Lurgi with ZSM-5 catalysts, mostly propylene is produced at yields above 70%. A process developed by ExxonMobil, with ZSM-5 catalyst, produces hydrocarbons in the gasoline and/or distillate range at selectivity greater than 95%.

There is also a methanol to gasoline (MTG) process, in which medium-pore zeolites with considerable acidity, e.g., ZSM-5, are used as catalysts. In this process, methanol is first dehydrated to an equilibrium mixture of dimethyl ether, methanol and water over a catalyst, and this mixture is then converted to light olefins, primarily ethylene and propylene. The light olefins can undergo further transformations to higher olefins, $C_3$-$C_6$ alkanes, and $C_6$-$C_{10}$ aromatics such as toluene, xylenes, and trimethylbenzene.

With decreasing oil and gas reserves, it is inevitable that synthetic hydrocarbons would play a major role. Thus, methanol-based synthetic hydrocarbons and chemicals available through MTG and MTO processes will assume increasing importance in replacing oil and gas-based materials. The listed uses of methanol is only illustrative and not limiting.

Methanol can also be used as a source of single cell proteins. A single cell protein (SCP) refers to a protein produced by a microorganism which degrades hydrocarbon substrates while gaining energy. The protein content depends on the type of microorganism, e.g., bacteria, yeast, mold, etc. The SCP has many uses, including uses as food and animal feed.

Considering the numerous uses of methanol, it is clearly desirable to have improved and efficient methods of producing methanol. Currently, methanol is almost exclusively made from synthesis gas obtained from incomplete combustion (or catalytic reforming) of fossil fuel, mainly natural gas (methane) and coal.

Methanol can also be made from renewable biomass, but such methanol production also involves syn-gas and may not be energetically favorable and limited in terms of scale. As used herein, the term "biomass" includes any type of plant or animal material, i.e., materials produced by a life form, including wood and wood wastes, agricultural crops and their waste byproducts, municipal solid waste, animal waste, aquatic plants, and algae. The method of transforming biomass to methanol is similar to the method of producing methanol from coal, and requires gasification of biomass to syn-gas, followed by methanol synthesis by the same processes used with fossil fuel. Use of biomass also presents other disadvantages, such as low energy density and high cost of collecting and transporting bulky biomass. Although recent improvements involving the use of "biocrude," black liquid obtained from fast pyrolysis of biomass, is somewhat promising, more development is needed for commercial application of biocrude.

The presently existing method of producing methanol involves syn-gas. Syn-gas is a mixture of hydrogen, carbon monoxide and carbon dioxide, and produces methanol over a heterogeneous catalyst according to the following equations:

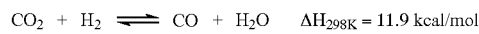

The first two reactions are exothermic with heat of reaction equal to $-21.7$ kcal.mol$^{-1}$ and $-9.8$ kcal.mol$^{-1}$, respectively, and result in a decrease in volume. Conversion to methanol is favored by increasing the pressure and decreasing the temperature according to Le Chatelier's principle. The third equation describes the endothermic reverse water gas shift reaction (RWGSR). Carbon monoxide produced in the third reaction can further react with hydrogen to produce methanol. The second reaction is simply the sum of the first and the third reactions. Each of these reactions is reversible, and is therefore limited by thermodynamic equilibrium under the reaction conditions, e.g., temperature, pressure and composition of the syn-gas.

Synthesis gas for methanol production can be obtained by reforming or partial oxidation of any carbonaceous material, such as coal, coke, natural gas, petroleum, heavy oil, and asphalt. The composition of syn-gas is generally characterized by the stoichiometric number S, corresponding to the equation shown below.

$$S = \frac{(\text{moles } H_2 - \text{moles } CO_2)}{(\text{moles } CO + \text{moles } CO_2)}$$

Ideally, S should be equal to or slightly above 2. A value above 2 indicates excess hydrogen, while a value below 2 indicates relative hydrogen deficiency. Reforming of feedstock having a higher H/C ratio, such as propane, butane or naphthas, leads to S values in the vicinity of 2, ideal for conversion to methanol. When coal or methane is used, however, additional treatment is required to obtain an optimal S value. Synthesis gas from coal requires treatment to avoid formation of undesired byproducts. Steam reforming of methane yields syn-gas with a stoichiometric number of 2.8 to 3.0, and requires lowering the S value closer to 2 by adding $CO_2$ or using excess hydrogen in some other process such as ammonia synthesis. However, natural gas is still the preferred feedstock for methanol production because it offers high hydrogen content and, additionally, the lowest energy consumption, capital investment and operating costs. Natural gas also contains fewer impurities such as sulfur, halogenated compounds, and metals which may poison the catalysts used in the process.

The existing processes invariably employ extremely active and selective copper-based catalysts, differing only in the reactor design and catalyst arrangement. Because only part of syn-gas is converted to methanol after passing over the catalyst, the remaining syn-gas is recycled after separation of methanol and water. There is also a more recently developed liquid phase process for methanol production, during which syn-gas is bubbled into liquid. Although the existing processes have methanol selectivity greater than 99% and energy efficiency above 70%, crude methanol leaving the reactor still contains water and other impurities, such as dissolved gas (e.g., methane, CO, and $CO_2$), dimethyl ether, methyl formate, acetone, higher alcohols (ethanol, propanol, butanol), and long-chain hydrocarbons. Commercially, methanol is available in three grades of purity: fuel grade, "A" grade, generally used as a solvent, and "AA" or chemical grade. Chemical grade has the highest purity with a methanol content exceeding 99.85% and is the standard generally observed in the industry for methanol production. The syn-gas generation and purification steps are critical in the existing processes, and the end result would largely depend on the nature and purity of the feedstock. To achieve the desired level of purity, methanol produced by the existing processes is usually purified by sufficient distillation. Another major disadvantage of the existing process for producing methanol through syn-gas is the energy requirement of the first highly endothermic steam reforming step. The process is also inefficient because it involves transformation of methane in an oxidative reaction to carbon monoxide (and some $CO_2$), which in turn must be reduced to methanol.

It is clearly desirable and advantageous to produce methanol without first producing syn-gas. It would be further advantageous to use an abundant, practically unlimited resource such as carbon dioxide as the carbon source to produce methanol. For example, U.S. Pat. No. 5,928,806, the entire content of which is incorporated herein by reference thereto, discloses production of methanol, and related oxygenates and hydrocarbons, based on a carbon dioxide-based regenerative fuel cell concept.

When hydrocarbons are burned they produce carbon dioxide and water. It is clearly of great significance, if this process can be reversed and an efficient and economic process can be found to produce methanol from carbon dioxide and water to be subsequently used for energy storage, fuels and production of synthetic hydrocarbons. In plant photosynthesis, carbon dioxide is captured from the air and converted with water and solar energy into new plant life. Conversion of plant life into fossil fuel, however, is a very long process. Thus, it is highly desirable to develop a process for chemical recycling carbon dioxide to produce hydrocarbon in a short, commercially feasible time scale.

Carbon dioxide is known to be photochemically or electrochemically readily reduced to formic acid with formaldehyde and methanol being formed in only smaller amounts. Direct electrochemical reduction of $CO_2$ into methanol under pressure also provides methyl formate. Catalytic hydrogenation of carbon dioxide using heterogeneous catalysts provides methanol together with water as well as formic acid and formaldehyde. As the generation of needed hydrogen is highly energy consuming, the production of methanol with equimolar amount of water as well as other side products from carbon dioxide is not practical. No efficient ways for the selective high yield, high selectivity economical conversion of carbon dioxide to methanol is presently known. The high selectivity laboratory reduction of carbon dioxide to methanol with complex metal hydrides, such as lithium aluminum hydride is extremely costly and therefore not suited for the bulk production of methanol.

Attempts have been made to chemically convert $CO_2$ to methanol and subsequently to a hydrocarbon by catalytic or electrochemical hydrogenation. Catalysts based on metals and their oxides, in particular copper and zinc, have been developed for this process. These catalysts are unexpectedly similar to the ones currently used for the conventional methanol production via syn-gas. It is now understood that methanol is most probably formed almost exclusively by hydrogenation of $CO_2$ contained in syn-gas on the surface of the catalyst. To be converted to methanol, CO present in the syn-gas first undergoes a water gas shift reaction to form $CO_2$ and $H_2$, and the $CO_2$ then reacts with hydrogen to produce methanol. One of the limiting factors for large scale use of such methanol conversion process is the availability of the feedstock, i.e., $CO_2$ and $H_2$. While $CO_2$ can be obtained relatively easily in large amounts from various industrial exhausts, hydrogen is mainly produced from non-renewable fossil fuel-based syn-gas and therefore has limited availability. Further, generation of hydrogen from fossil fuels has a high energy requirement.

Other methods for hydrogen production from fossil fuel have been investigated, including the "Carnol" process, in which thermal decomposition of methane produces hydrogen and solid carbon. The generated hydrogen is then reacted with $CO_2$ to produce methanol. This process is advantageous over methane steam reforming for requiring relatively less energy, about 9 kcal for producing one mol of hydrogen, and for producing a byproduct that can be more easily handled, stored and used, compared to $CO_2$ emissions generated by methane steam reforming or partial oxidation. However, the thermal decomposition of methane requires heating it to temperatures of above 800° C. and gives only relatively low yield of hydrogen. The process, in any case, requires substantial development for commercial application.

If methanol could be produced on a large scale from recycling carbon dioxide, such a process would also be advantageous considering the abundant supply of carbon dioxide in the atmosphere and in industrial exhausts of fossil fuel power burning power plants and cement plants. It would at the same time also mitigate greenhouse effect that is causing the global climate change (i.e., global warming). The present invention now provides such a process to obtain these benefits.

SUMMARY OF THE INVENTION

The invention relates to various embodiments of an environmentally beneficial method for producing methanol by reductive conversion of an available source of carbon dioxide. A first embodiment includes the steps of reducing the carbon dioxide under conditions sufficient to produce a reaction mixture containing formic acid with concomitant formation of formaldehyde and small amounts of methanol and methane, followed, without separation of the reaction mixture, by a treatment step conducted under conditions sufficient to convert the formaldehyde to formic acid and methanol.

A second embodiment includes the steps of augmenting the reaction mixture of the process of the first embodiment by reacting the formaldehyde with some of the formic acid as a hydrogen source, without separation of the reaction mixture, into methanol, and by reacting some of the formic acid with methanol to form methyl formate, followed by catalytically hydrogenating the methyl formate under conditions sufficient to form methanol.

A third embodiment includes the steps of generating carbon monoxide from the carbon dioxide through a high temperature reaction with carbon, reacting the carbon monoxide with methanol produced by the process of the first embodiment under conditions sufficient to form methyl formate, followed by catalytic hydrogenation of the methyl formate under conditions sufficient to form methanol.

In any embodiment, the carbon dioxide can be conveniently obtained from an exhaust stream from fossil fuel burning power or industrial plant, or a source accompanying natural gas. The carbon dioxide obtained from such sources can be reduced by catalytic, photochemical or electrochemical reduction. Another convenient source of carbon dioxide is the atmosphere and it can be obtained by absorbing atmospheric carbon dioxide onto a suitable adsorbent followed by treating the adsorbent to release the adsorbed carbon dioxide therefrom. The adsorbent can be treated by sufficient heating or by being subjected to a sufficiently reduced pressure to release the adsorbed carbon dioxide.

When the carbon dioxide is first reduced to carbon monoxide with carbon, it can subsequently be reacted with methanol produced in the process of the first embodiment to obtain methyl formate, which then is then catalytically hydrogenated to produce methanol. The hydrogen needed for the hydrogenation of methyl formate is preferably obtained by decomposing at least some of the formic acid from the reaction mixture. Also, the hydrogen needed for the reduction of carbon dioxide can be provided reacting carbon dioxide with methane or natural gas. The reaction of methane with carbon dioxide can also provide hydrogen for the hydrogenation of the methyl formate.

To form other products, the methanol can be dehydrated under conditions sufficient to produce dimethyl ether. The dimethyl ether can be heated in the presence of an acidic-basic or zeolitic catalysts to form ethylene or propylene. The latter can be converted either to higher olefins, synthetic hydrocarbons or aromatics and their products for use as feedstocks for chemicals or as transportation fuels. Ethanol or propanol can be prepared by hydration of the ethylene or propylene, respectively. Alternatively, the dimethyl ether can be used as a substitute for natural gas and LPG for heating purposes for households or industrial use.

In the area of synthetic fuels, an improved diesel fuel can be prepared by mixing sufficient amounts of dimethyl ether with conventional diesel fuel. Also, dimethyl carbonate can be formed by reaction of the methanol with phosgene or by the oxidative carbonylation of the methanol, and an improved diesel fuel can be prepared by mixing sufficient amounts of dimethyl carbonate with conventional diesel fuel. A transportation fuel can be prepared by adding methanol to gasoline with the fuel having a minimum gasoline content of at least 15% by volume.

As to other uses, the methanol or dimethyl ether can act as convenient energy storage and transportation materials in order to minimize or eliminate the disadvantages or dangers inherent in the use and transportation of LNG or LPG. It is also possible to use the methanol for preparing single cell proteins for human or animal alimentation.

BRIEF DESCRIPTION OF THE DRAWINGS

The features and benefits of the invention will become more evident from review of the following detailed description of illustrative embodiments and the accompanying drawings, wherein.

DETAILED DESCRIPTION OF THE PREFERRED EMBODIMENTS

Figure 1:
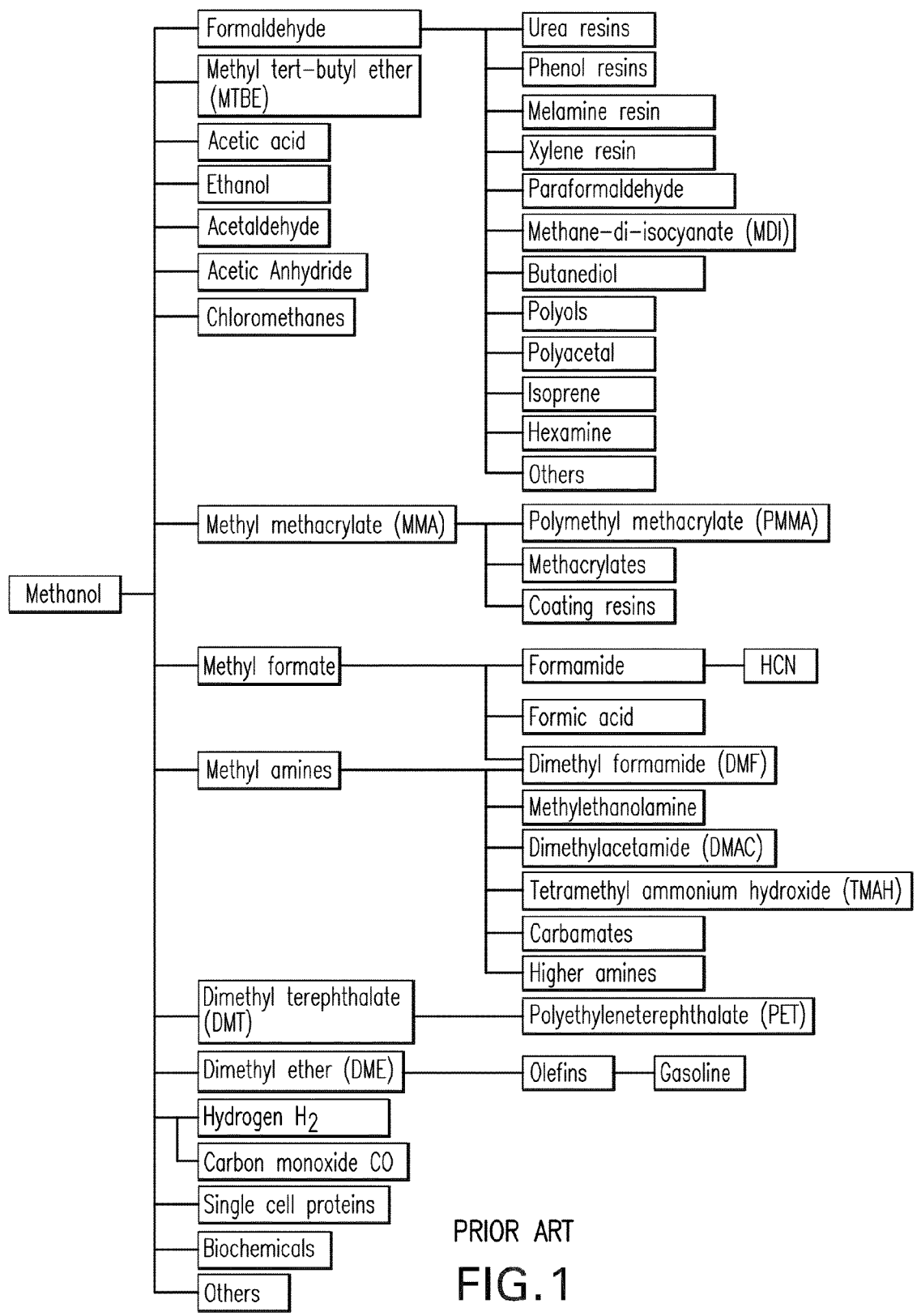
FIG. 1 shows known examples of methanol-derived chemical products and materials.
Figure 2:
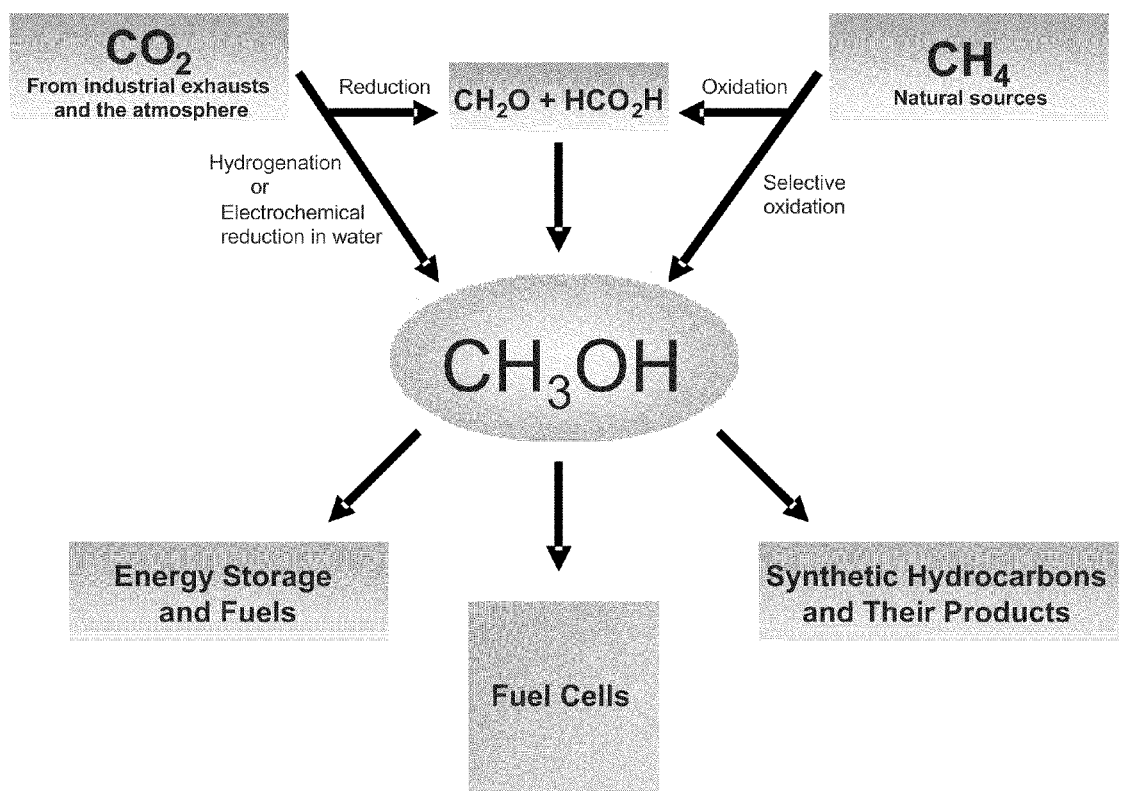
FIG. 2 schematically illustrates the present inventive process, termed the METHANOL ECONOMY process by inventor George Olah.

The present invention relates to the efficient and economical conversion of carbon dioxide from flue gases of fossil fuel burning power plants, industrial exhaust gases, $CO_2$ accompanying natural gas or from the atmosphere itself to methanol or dimethyl ether, with their subsequent application for energy storage and transportation fuels, conversion to synthetic hydrocarbons and their products, synthetic proteins and other products. The carbon dioxide to methanol conversion is a better alternative to sequestration, wherein carbon dioxide through methanol is converted to useful and essential products making it a renewable general carbon source for fuels, synthetic hydrocarbons and their products.

The present invention discloses an environmentally harmonius and efficient method of converting any carbon dioxide source to methanol. Suitable carbon dioxide sources can be industrial exhaust streams from hydocarbon (fossil fuel) burning power plants, cement plants natural gas wells, and the like, as well as the atmosphere. The use of this process of converting carbon dioxide to methanol and/or dimethyl ether and their products will also lead to a significant reduction of carbon dioxide, a major greenhouse gas, in the atmosphere thus mitigating global warming.

Carbon dioxide from the mentioned sources provides formic acid and some formaldehyde in good conversion by either photochemical or electrochemical reduction. Formic acid and formaldehyde thus produced, in a subsequent process step, can be substantially converted to methyl formate, which upon hydrogenation further yields exclusively methanol. The conversion of formaldehyde can be conducted in the presence of a solid supported basic catalyst or an organometallic catalyst to give methanol and formic acid and subsequently methyl formate. Alternatively, dimerization of formaldehyde gives methyl formate, which upon catalytic hydrogenation yields methanol as the only product.

Carbon dioxide is preferably obtained from mentioned high concentration sources of its generation prior to its release into the atmosphere. Carbon dioxide can, however, also be obtained by separating atmospheric carbon dioxide with a suitable adsorbent followed by desorption treatment to release the adsorbed carbon dioxide therefrom. This can be achieved by heating to release the adsorbed carbon dioxide, by treating it under reduced pressure or by a suitable combination of both.

In another embodiment of the invention, carbon dioxide is first thermally reduced with carbon to carbon monoxide, which is subsequently reacted with methanol to obtain methyl formate. Reduction of methyl formate then provides methanol in double its initial amount.

A further route to methanol is based on the use of methane or natural gas in the reductive conversion of carbon dioxide (dry reforming) to provide a mixture of carbon monoxide and hydrogen, which subsequently can react to produce methanol. As the reforming of carbon dioxide with methane generates hydrogen, this hydrogen can also be used for the hydrogenation of methyl formate to methanol in the previously discussed embodiments.

Methanol produced according to the discussed new processes can be used for any of the purposes such as for energy storage and transportation, as a fuel in internal combustion engines or fuel cells, to produce related fuels (dimethyl ether, by dehydration), dimethyl carbonate (by oxidative carbonylation), to produce ethylene, propylene, higher olefins, synthetic hydrocarbons and all their derived products including and not limiting single cell proteins.

The present invention relates to efficient new ways of converting varied carbon dioxide sources into methanol. High concentration carbon dioxide sources are those frequently accompanying natural gas in amounts of 5 to 50%, those from flue gases of fossil fuel (coal, natural gas, oil, etc.) burning power plants, exhaust of cement plants and other industrial sources. From the carbon dioxide mainly formic acid together with smaller amounts of formaldehyde can be readily obtained by either photochemical or electrochmical reduction while methanol formation is low. The present invention teaches that, without separation of the product mixture in a subsequent treatment step, the mixture can be converted to methanol making the overall process both selective and high yielding. In another embodiment, electrochemical reduction of carbon dioxide in methanol solution under pressure was found to provide high yield of methyl formate, which can subsequently hydrogenatively converted exclusively into methanol. In a further embodiment, the high temperature reaction of carbon with carbon dioxide produces carbon monoxide, which upon reaction with methanol gives methyl formate for further conversion to methanol. In this embodiment the initial reduction of carbon dioxide is affected instead of hydrogen by carbon (coal) thus decreasing the overall amount of hydrogen needed for producing methanol.

The present invention discloses the efficient and economical conversion of carbon dioxide, either from flue gases or fossil fuel burning power plants, from natural gas wells, varied industrial exhaust gases or from the atmosphere itself, to methanol. As catalytic, photochemical or electrochemical reduction of carbon dioxide preferentially produces formic acid, with some formaldehyde and methanol, the present invention is based on a subsequent efficient conversion step of the reduction product mixtures to methanol in good overall yield and selectivity. The environmental and economic benefits of reductive chemical reaction of carbon dioxide emission instead of sequestration are a significant part of the present invention. At the same time, carbon dioxide provides a renewable source of methanol (together with dimethyl ether) that can be used for safe energy storage and transportation, transportation fuel, fuel for fuel cells, fuel additive or feedstock for producing other compounds, polymers, plastics or related materials.

The use of carbon dioxide based methanol is highly desirable as it can mitigate and eventually replace the world's reliance on fossil fuels. In addition, the reduction in carbon dioxide emissions as well as the removal of excess carbon dioxide from the atmosphere will assist in reducing global warming and restoring atmospheric conditions to a preindustrial levels, thus preserving the planet's climate for future generations.

The present invention overcomes the major difficulties in economically converting carbon dioxide to methanol. As indicated, electrochemical or photochemical reduction of $CO_2$ mainly produces formic acid and formaldehyde. According to the present invention, formic acid and formaldehyde can be converted, in a subsequent step, to methanol with formic acid providing the needed hydrogen. Using suitable catalytic conditions, formic acid can be used for the chemical reduction of formaldehyde (as a source of hydrogen) to methanol and carbon dioxide, the latter which can be recycled into the reductive process.

$$HCHO + HCO_2H \rightarrow CH_3OH + CO_2$$

At the same time formic acid can be thermally or catalytically cleaved to produce hydrogen for use in catalytic hydrogenation to produce methanol.

$$HCOOH \rightarrow H_2 + CO_2$$

As well known, formic acid reacts with methanol to produce methyl formate. Methyl formate subsequently can be efficiently catalytically hydrogenated to give exclusively methanol, allowing complete utilization of the used hydrogen in producing only the desired product.

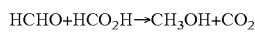
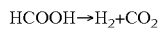

The specific conditions for the foregoing individual reactions are generally known to the skilled chemists and optimum conditions can be readily established for specific sequences of the disclosed overall processes to produce methanol.

Methyl formate can also be directly produced by the electrochemical reduction of carbon dioxide in methanol solution under pressure.

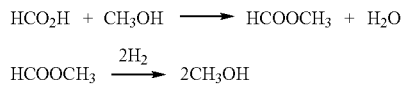

Formic acid can also be used as the hydrogen source for the reduction of methyl formate to methanol over noble metal catalysts.

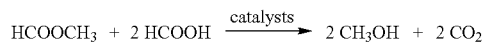

Otherwise, hydrogen used in catalytic hydrogenation can be obtained from any suitable source, such as electrolysis of water, using any suitable method and source of energy, e.g., atomic, solar, wind, geothermal, etc. Photolytic, thermal, enzymatic, and other means of cleavage of water to hydrogen is also possible.

Another embodiment of the present invention utilizes the known process that methyl formate can be made from CO and methanol. However, instead of using synthesis gas as a source of carbon monoxide, it can be efficiently made by reacting carbon dioxide with carbon at elevated temperatures (Boudouard reaction).

$$CO_2 + C \rightarrow 2\ CO$$

CO thus produced, when reacted with methanol gives methyl formate, which by aforementioned hydrogenation results in doubling the amount of the used methanol with no other by product.

In this embodiment, the initial reduction of carbon dioxide to carbon monoxide is carried out with carbon, thus lowering the amount of needed energy to produce hydrogen, which otherwise is partially used to produce water in the hydrogenation of carbon dioxide.

Carbon dioxide can further also be used in the dry catalytic reforming of methane, if natural gas is available, producing carbon monoxide and hydrogen to be used to produce methanol.

$$CH_4 + CO_2 \rightarrow CO + 2H_2$$

As shown initially by Bagno, Bukala and Olah (J. Org. Chem. 1990, 55, 4284) methanol (dimethyl ether) and CO can under superacidic catalytic conditions also be used to produce acetic acid. It is thus possible to react carbon dioxide and methane to produce acetic acid and through it a wide variety of industrially valuable products.

The skilled chemist is again familiar with the general conditions for carrying out the individual reactions and thus to find the optimal conditions for desired sequences.

$CO_2$ emissions from fossil fuel burning power plants and varied industries can be captured on-site. Separation of $CO_2$ from such industrial exhausts is well-developed. The major advantage in the newly disclosed chemical recycling of these sources to methanol and derived products is that carbon dioxide is not released into the atmosphere and serves as renewable carbon source for fuels and varied essential products.

The capture and use of existing atmospheric $CO_2$ allows chemical recycling of $CO_2$ as a renewable and unlimited source of carbon. $CO_2$ absorption facilities can be placed proximate to a hydrogen production site to enable subsequent methanol synthesis. Although the $CO_2$ content in the atmosphere is low (only 0.037%), the atmosphere offers an abundant and unlimited supply because $CO_2$ is recycled. For using atmospheric carbon dioxide efficiently, $CO_2$ absorption facilities are needed. This can be addressed by using efficient $CO_2$ absorbents such as polyethyleneimines, polyvinylpyridines, polyvinylpyrroles, etc., on suitable solid carriers (e.g., active carbon, polymer, silica or alumina), which allow absorbtion of even the low concentration of atmospheric $CO_2$. $CO_2$ can also be captured using basic absorbents such as calcium hydroxide $(Ca(OH)_2)$ and potassium hydroxide (KOH), which react with $CO_2$ to form calcium carbonate $(CaCO_3)$ and potassium carbonate $(K_2CO_3)$, respectively. $CO_2$ absorption is an exothermic reaction, which liberates heat, and is readily achieved by contacting $CO_2$ with an adequate base. After capture, $CO_2$ is recovered from the absorbent by desorption, through heating, vacuum (or reduced pressure) or electrochemical treatment. Calcium carbonate, for example, is thermally calcinated to release carbon dioxide. As desorption is an endothermic, energy-demanding step, the appropriate treatment can be chosen to optimize absorption and desorption with the lowest possible energy input. Thus, $CO_2$ can be recycled by operation of absorbing-desorbing columns in convenient cycles with modest heating and/or under reduced pressure to cause desorption of $CO_2$ to take place.

When methanol, methanol-derived fuels or synthetic hydrocarbons are combusted (oxidatively used), they release $CO_2$ and water, thus providing the basis methanol cycle, the artificial version of the natural recylcing of $CO_2$. In contrast to the nonrenewable fossil fuel sources such as oil, gas, and coal recycling carbon dioxide from industrial and natural sources to produce methanol not only addresses the problem of diminishing fossil fuel resources, but also helps alleviate global warming due to greenhouse effect, which is significantly caused by mankind's activity that is increasing the carbon dioxide content in the atmosphere.

The effective hydrogenative recycling of carbon dioxide disclosed herein provides new methods of producing methanol in an improved, efficient, and environmentally beneficial way, while mitigating $CO_2$ caused climate change (global warming). The use of methanol and derived dimethyl ether as energy storage and transportation materials eliminates many difficulties of using hydrogen for such purposes. They are also convenient transportation fuels and as raw materials for producing synthetic hydrocarbons and their related products. The safety and versatility of methanol makes the disclosed recycling of carbon dioxide further desirable.

As known in the art, methanol can be easily treated to produce varied derived compounds including dimethyl ether, produced by dehydration of methanol, and dimethyl carbonate, produced by reaction of the methanol by oxidative carbonylation. Methanol and methanol-derived compounds, e.g., DME and DMC as oxygenated additives, can be blended with gasoline and used in internal combustion engines with only minor modifications. For example, methanol can be added to gasoline up to 85% by volume to prepare M85 fuel. Methanol can also be used to generate electricity in fuel cells, by either first catalytically reforming methanol to $H_2$ and CO or by reacting methanol directly with air in a direct methanol fuel cell (DMFC). DMFC greatly simplifies the fuel cell technology and makes it readily available to a wide range of applications, including portable mobile electronic devices and electricity generators.

In addition to being a conveniently storable energy source and fuel, methanol and methanol-derived DME and DMC are useful starting materials for various chemicals such as formaldehyde, acetic acid, and a number of other products including polymers, paints, adhesives, construction materials, synthetic chemicals, pharmaceuticals, and single cell proteins.

Methanol and/or dimethyl ether can also be conveniently converted in a single catalytic step to ethylene and/or propylene (e.g., in a methanol to olefin or MTO process), the building blocks for producing synthetic hydrocarbons and their products. This means that the hydrocarbon fuels and products currently derived from oil and natural gas can be obtained from methanol, which itself can advantageously be obtained from simple chemical recycling of atmospheric or industrial $CO_2$ sources. An other utlization of methanol is its ready conversion to ethanol via hydration of derived ethylene. Many further applications are known and can be applied to carbon dioxide derived methanol. It should be emphasized that there is no preference for any particular energy source needed for producing methanol. All sources, including alternative sources and atomic energy can be used. Energy once produced must be, however, stored and transported, for which methanol is well suited.

The improved and efficient selective conversion of carbon dioxide, which can be from atmospheric or industrial exhaust sources, to methanol according to the present invention also provides the needed raw material for what the inventors have termed the METHANOL ECONOMY process. This allows convenient storage and transport of energy in a liquid product that can be used as a fuel in internal combustion engines or in fuel cells and as a starting material for synthetic hydrocarbons and their varied products. The METHANOL ECONOMY process is based on the efficient direct conversion of still available natural gas resources to methanol or dimethyl ether (as disclosed in U.S. patent application Ser. No. 11/402,051, filed on Apr. 6, 2006, the entire content of which is incorporated herein by reference thereto) and the presently disclosed reductive chemical conversion of carbon dioxide. The concept of the METHANOL ECONOMY process presents significant advantages and possibilities. In the METHANOL ECONOMY process, methanol is used as (1) convenient energy storage medium, which allows convenient and safe storage and handling; (2) readily transported and dispensed fuel, including for methanol fuel cells; and (3) feedstock for synthetic hydrocarbons and their products currently obtained from oil and gas resources, including polymers and even single cell proteins, which can be used for animal feed or human consumption. The environmental benefits obtained by disclosed chemical recycling of carbon dioxide results in mitigating the global warming to ensure the well being of future generations.

As methanol is readily dehydrated to dimethyl ether, the disclosed conversion of carbon dioxide to methanol is also adaptable to produce dimethyl ether for fuel and chemical applications as previously noted.

The disclosed new efficient production of methanol from industrial or natural carbon dioxide sources, or even from the air itself, provides the needed raw material for replacing the diminishing fossil fuel through the METHANOL ECONOMY process. The conversion of carbon dioxide to methanol necessitate significant energy, which can be, however, provided by any energy source including offpeak electric power of fossil fuel (e.g., coal) burning power plants, atomic energy or any alternative energy sources (solar, wind, geothermal, hydro, etc.). As indicated, energy generated, however, must be conveniently stored and transported. The reduction of $CO_2$ to methanol allows storage and transportation of energy in a convenient liquid product (i.e., methanol) more convenient, economical and safe than volatile hydrogen gas. Methanol and/or dimethyl ether are efficient fuels in internal combustion engines or in direct oxidation methanol fuel cells (DMFC as well as raw materials for olefins, synthetic hydrocarbons and varied products. The present invention greatly extends the scope of the utilization of carbon dioxide for the production of methanol and/or dimethyl ether from natural or industrial sources, even from the air itself.

EXAMPLES

The following examples illustrate but not limit the utility of the present process. They are based on the use of known suitable or modified chemical reactions that are applied to the processes of the invention.

Example 1

Carbon dioxide is known to be electrochemically reducible to formic acid and formaldehyde in aqueous media over Sn, Pb, In, Zn, Au, Cu, Pd and related electrodes at room temperature in the range of 40-90% current efficiency, while the formation of methanol and methane is significantly low.

The mixture of formic acid and formaldehyde can be passed over $WO_3/Al_2O_3$ in a qartz tube reactor at 190° C. Methanol and methyl formate are then obtained in overall yield of about 40%, while the utilization of formic acid is about 70%. When the reaction of formaldehyde and formic acid in water is carried out at 250° C. in a glass lined reactor, methanol is obtained at a yield of about 60%.

Example 2

Carbon dioxide can be reacted with carbon at elevated temperatures to produce carbon monoxide in the Boudouard reaction. It then can be reacted with methanol to give methyl formate which then can be hydrogenatively converted to produce methanol.

Example 3

The methyl formate obtained by the processes of Examples 1 and 2 is catalytically reduced with molecular hydrogen in the gas phase over copper chromite or nobel metal catalysts at atmospheric pressure in the temperature range of 100-230° C. Selectivity to methanol is >90% and methyl formate conversion is about 85 to 90%. A similar reductive conversion can also be achieved electrochemically.

Example 4

Methyl formate is catalytically reduced with formic acid over Pt/C, Rh/C, Ru/C, copper chromite and the like catalysts in the gas phase at atmospheric pressure in the temperature range of 100-200° C. Selectivity to methanol is over 70-90% and methyl formate conversion is 50% in a single pass.

Example 5

Methane is reacted with carbon dioxide to give a 1:2 mixture of carbon monoxide and hydrogen under "dry" reforming conditions. This mixture is subsequently used to produce methanol. The carbon monoxide formed can also react with methanol itself to give methyl formate, which according to Examples 3 and 4 can be hydrogenatively converted doubling the amount of methanol under mild reaction conditions (moderate temperatures and pressures).

These examples illustrate the general utility of the present process but skilled practitioners can utilize the disclosure and teachings provided herein to generate a wide variety of chemicals and products that in addition to reducing reliance on fossil fuels will also enhance the environment by significantly reducing carbon dioxide emissions and the presence of carbon dioxide in the atmosphere.

What is claimed is:

1. An environmentally beneficial method of reducing the carbon dioxide content of the atmosphere by recycling carbon dioxide and producing methanol using a reductive conversion of an available source of carbon dioxide that is present in or would otherwise be discharged into the atmosphere, which method comprises:

(A) reducing the carbon dioxide under conditions sufficient to produce a reaction mixture containing formic acid with concomittant formation of formaldehyde and small amounts of methanol and methane, followed, without separation of the reaction mixture, by a treatment step conducted under conditions sufficient to convert the formaldehyde to formic acid and methanol; or (B) augmenting the reaction mixture of (A) by reacting the formaldehyde with some of the formic acid as a hydrogen source, without separation of the reaction mixture, into methanol, and by reacting some of the formic acid with methanol to form methyl formate, followed by catalytically hydrogenating the methyl formate under conditions sufficient to form methanol; or (C) generating carbon monoxide from the carbon dioxide through a high temperature reaction with carbon, reacting the carbon monoxide with methanol produced in (A) under conditions sufficient to form methyl formate, followed by catalytic hydrogenation of the methyl formate under conditions sufficient to form methanol.

2. The method of claim 1, wherein the carbon dioxide is obtained from an exhaust stream from fossil fuel burning power or industrial plant, or a source accompanying natural gas, and the carbon dioxide obtained from such sources is reduced by catalytic, photochemical or electrochemical reduction.

3. The method of claim 1, wherein the available carbon dioxide source is the atmosphere and the carbon dioxide is obtained by absorbing atmospheric carbon dioxide onto a suitable adsorbent followed by treating the adsorbent to release the adsorbed carbon dioxide therefrom.

4. The method of claim 3, wherein the adsorbent is treated by sufficient heating to release the adsorbed carbon dioxide.

5. The method of claim 3, wherein the adsorbent is treated by subjecting the adsorbent to sufficient reduced pressure to release the adsorbed carbon dioxide.

6. The method of claim 3, wherein the carbon dioxide is first reduced to carbon monoxide with carbon, reacted subsequently with methanol produced in step (A) to obtain methyl formate, and then catalytically hydrogenating the methyl formate to produce methanol.

7. The method of claim 1, wherein the hydrogen needed for the hydrogenation of methyl formate is obtained by decomposing at least some of the formic acid from the reaction mixture.

8. The method of claim 1, wherein the hydrogen needed for the reduction of carbon dioxide is provided reacting carbon dioxide with methane or natural gas.

9. The method of claim 7, wherein the reaction of methane with carbon dioxide provides hydrogen for the hydrogenation of the methyl formate.

10. The method of claim 1 which further comprises dehydrating methanol under conditions sufficient to produce dimethyl ether.

11. The method of claim 10 which further comprises heating dimethyl ether in the presence of an acidic-basic or zeolitic catalysts to form ethylene or propylene.

12. The method of claim 11 which further comprises converting ethylene or propylene either to higher olefins, synthetic hydrocarbons or aromatics and their products, for use as feedstocks for chemicals or as transportation fuels.

13. The method of claim 11 which further comprises hydrating ethylene or propylene to form ethanol or propanol.

14. The method of claim 10 wherein the dimethyl ether is used as a substitute for natural gas and LPG for heating purposes for households or industrial use.

15. The method of claim 10 which further comprises preparing an improved diesel fuel by mixing sufficient amounts of dimethyl ether with conventional diesel fuel.

16. The method of claim 1 which further comprises forming dimethyl carbonate by reaction of the methanol with phosgene or by oxidative carbonylation of the methanol.

17. The method of claim 16 which further comprises preparing an improved diesel fuel by mixing sufficient amounts of dimethyl carbonate with conventional diesel fuel.

18. The method of claim 1 which further comprises preparing transportation fuel by adding methanol to gasoline with the fuel having a minimum gasoline content of at least 15% by volume.

19. The method of claim 10 which further comprises utilizing the methanol or dimethyl ether as convenient energy storage and transportation materials in order to minimize or eliminate the disadvantages or dangers inherent in the use and transportation of LNG or LPG.

20. The method of claim 10 which further comprises utilizing the methanol for preparing single cell proteins for human or animal alimentation.

* * * * *

UNITED STATES PATENT AND TRADEMARK OFFICE
CERTIFICATE OF CORRECTION

| | | |
|---|---|---|
| PATENT NO. | : 7,605,293 B2 | Page 1 of 1 |
| APPLICATION NO. | : 11/402050 | |
| DATED | : October 20, 2009 | |
| INVENTOR(S) | : Olah et al. | |

It is certified that error appears in the above-identified patent and that said Letters Patent is hereby corrected as shown below:

Title Page:
Item (57) ABSTRACT, at line 3, change "powerplants," to -- power plants, --; and at line 5, delete the second occurrence of "acid".

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,605,293 B2  Page 1 of 1
APPLICATION NO. : 11/402050
DATED : October 20, 2009
INVENTOR(S) : Olah et al.

It is certified that error appears in the above-identified patent and that said Letters Patent is hereby corrected as shown below:

Column 2:
Line 53, change "bums" to -- burns --.

Column 9:
Line 40, change "a hydrocarbon" to -- hydrocarbons --.

Column 14:
Line 39, change the equation "$CH_4 + CO_2 \longrightarrow CO + 2H_2$" to
-- $CH_4 + CO_2 \longrightarrow 2CO + 2H_2$ --.

Column 17:
Line 55, change "1:2" to -- 1:1 --.

Signed and Sealed this

Sixteenth Day of November, 2010

David J. Kappos
*Director of the United States Patent and Trademark Office*